US010585917B2

(12) United States Patent
Melvin et al.

(10) Patent No.: US 10,585,917 B2
(45) Date of Patent: Mar. 10, 2020

(54) REAL TIME DATA TRACKING, ANALYTICS DATA WAREHOUSING, AND FRONT END REPORTING SYSTEM

(71) Applicant: TeleTracking Technologies, Inc., Pittsburgh, PA (US)

(72) Inventors: Shawn M. Melvin, Pittsburgh, PA (US); Tara Bosco Lynch, Pittsburgh, PA (US); Nadezda Mirkova, Pittsburgh, PA (US); Michael L. Nacey, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 392 days.

(21) Appl. No.: 15/298,642

(22) Filed: Oct. 20, 2016

(65) Prior Publication Data

US 2017/0116381 A1     Apr. 27, 2017

Related U.S. Application Data

(60) Provisional application No. 62/245,440, filed on Oct. 23, 2015.

(51) Int. Cl.
*G06F 16/28*        (2019.01)
*G16H 40/63*        (2018.01)
(Continued)

(52) U.S. Cl.
CPC ........ *G06F 16/283* (2019.01); *G06F 16/2423* (2019.01); *G06F 16/26* (2019.01); *G16H 40/20* (2018.01); *G16H 40/63* (2018.01)

(58) Field of Classification Search
CPC .. G06F 15/025; G06F 17/30477; G06F 9/451; G06F 17/30067; H04L 41/5006; G06Q 40/00; G16H 10/60
See application file for complete search history.

(56) References Cited

U.S. PATENT DOCUMENTS

| 8,499,331 B1* | 7/2013 | Yehuda | ............... H04L 41/5006 |
| | | | 709/223 |
| 2004/0122756 A1* | 6/2004 | Creeden | ................. G06Q 40/00 |
| | | | 705/35 |

(Continued)

FOREIGN PATENT DOCUMENTS

| WO | 0068842 A1 | 11/2000 |
| WO | 2014204994 A1 | 12/2014 |

OTHER PUBLICATIONS

Search Report for European Patent Application No. EP16194838, 3 pages, The Hague, Netherlands.

*Primary Examiner* — Toan H Vu
(74) *Attorney, Agent, or Firm* — Ference & Associates LLC

(57) ABSTRACT

An embodiment provides a method, including: receiving, from a plurality of devices, event data; storing, in electronic memory of one or more source devices, event data reported by the plurality of devices; routing, using a processor, the event data to a warehouse database; storing, in the warehouse database, the event data according to a plurality of storage dimensions associated with one or more of a plurality of selectable elements of a graphical user interface; and displaying, on a display device operatively coupled to the warehouse database, a front end program comprising the graphical user interface having the plurality of selectable elements; wherein, responsive to user interface with one of the plurality of selectable elements in the graphical user interface, the data warehouse communicates a subset of the event data by associating a storage dimension with the one of the selectable elements in the graphical user interface. Other embodiments are described and claimed.

20 Claims, 18 Drawing Sheets

(51) Int. Cl.
    *G16H 40/20*     (2018.01)
    *G06F 16/242*     (2019.01)
    *G06F 16/26*     (2019.01)

(56) References Cited

U.S. PATENT DOCUMENTS

| | | | |
|---|---|---|---|
| 2007/0033172 A1* | 2/2007 | Williams | G06F 17/30067 |
| 2008/0163085 A1* | 7/2008 | Subbu | G06F 9/451 |
| | | | 715/763 |
| 2009/0177988 A1 | 7/2009 | Martins | |
| 2009/0222539 A1* | 9/2009 | Lewis | G06F 19/3481 |
| | | | 709/221 |
| 2013/0042197 A1* | 2/2013 | Amare | G06F 15/025 |
| | | | 715/777 |
| 2014/0350966 A1* | 11/2014 | Khatana | G16H 10/60 |
| | | | 705/3 |
| 2017/0139996 A1* | 5/2017 | Marquardt | G06F 17/30477 |

\* cited by examiner

REAL TIME DATA TRACKING, ANALYTICS DATA WAREHOUSING, AND FRONT END REPORTING SYSTEM

CROSS REFERENCE TO RELATED APPLICATIONS

This application claims priority to U.S. Provisional Application Ser. No. 62/245,440, filed on Oct. 23, 2015, the contents of which are incorporated by reference herein.

BACKGROUND

Healthcare systems and facilities require data availability, e.g., in order to analyze processes and improve performance, particularly in the management of their healthcare operations. In a conventional technique, data of interest (e.g., number of admissions, average times for a patient in hospital, etc.) are recorded and stored. Typically this permitted record-by-record transactional data to be made available. However, extracting useful information remains time consuming using such an approach and determining useful characteristics (e.g., trends, achievement of milestones or goals, etc.) from such data required a large amount of manual input.

This difficulty in turn led to the generation of some standard reports, prepared via automatically processing the transactional data and forming a standard report. Systems generating such standard reports materially improved the ability of administrators and other decision makers to understand the transaction data and make use of it.

BRIEF SUMMARY

In summary, one embodiment provides a system, comprising: a plurality of devices that provide event data; one or more source devices that store, in electronic memory, the event data provided by the plurality of devices; a processor that operates to route the event data to a warehouse database; said warehouse database storing the event data according to a plurality of storage dimensions associated with one or more of a plurality of selectable elements of a graphical user interface; and a front end program that displays the graphical user interface having the plurality of selectable elements; wherein, responsive to user interface with one of the plurality of selectable elements in the graphical user interface, the data warehouse communicates a subset of the event data by associating a storage dimension with the one of the selectable elements in the graphical user interface.

Another embodiment provides a method, comprising: receiving, from a plurality of devices, event data; storing, in electronic memory of one or more source devices, event data reported by the plurality of devices; routing, using a processor, the event data to a warehouse database; storing, in the warehouse database, the event data according to a plurality of storage dimensions associated with one or more of a plurality of selectable elements of a graphical user interface; and displaying, on a display device operatively coupled to the warehouse database, a front end program comprising the graphical user interface having the plurality of selectable elements; wherein, responsive to user interface with one of the plurality of selectable elements in the graphical user interface, the data warehouse communicates a subset of the event data by associating a storage dimension with the one of the selectable elements in the graphical user interface.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
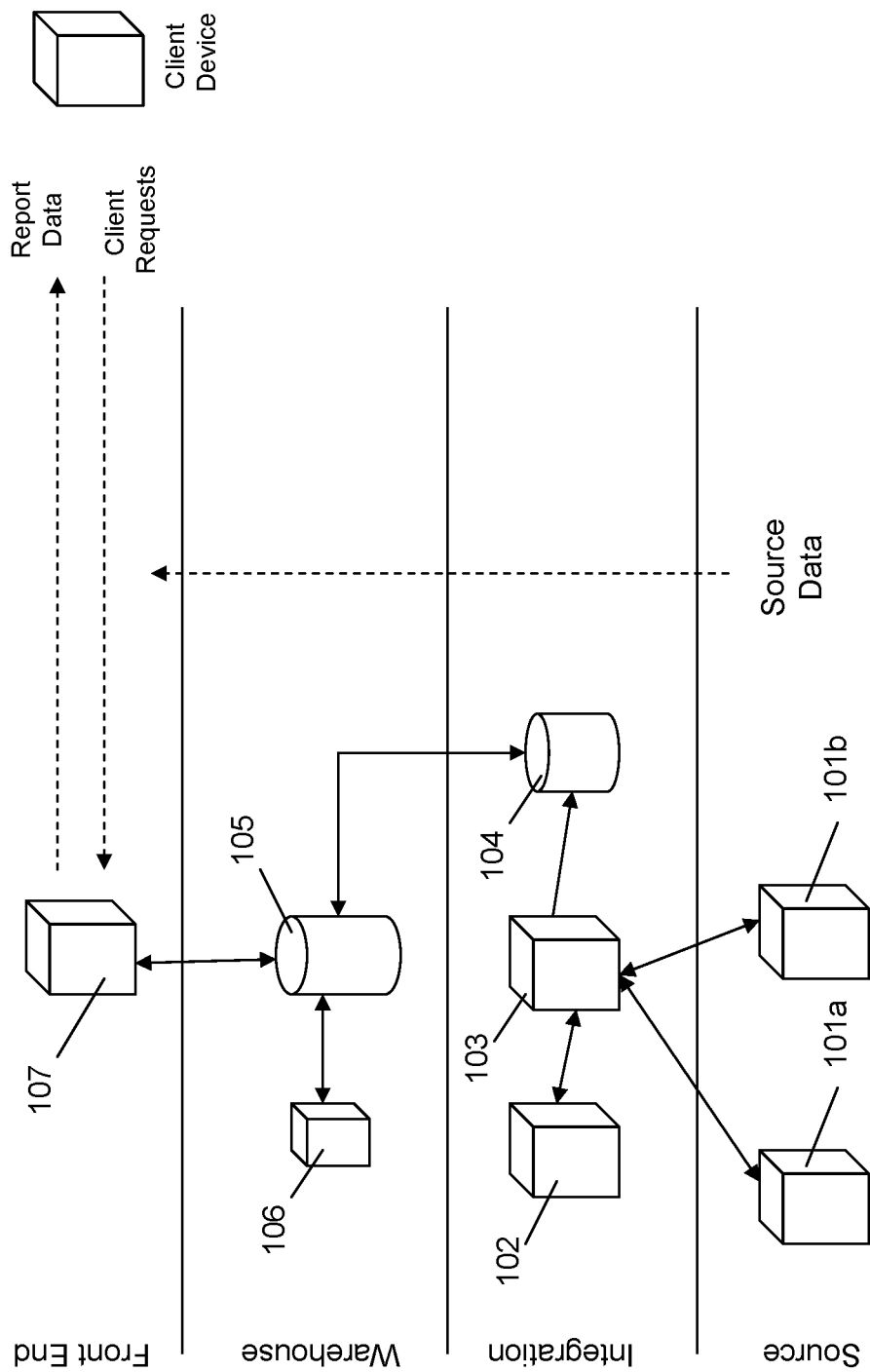
FIG. 1 illustrates an example of system architecture according to an embodiment.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation.

Systems generating standard reports materially improved the ability of administrators and other decision makers to understand certain record-by-record transactional data and make use of it. However, using standard reports included several drawbacks. For example, the standard report set may not have included the report type desired by a particular user. Thus, if the data presentation was not included in the standard set of reports, users were left to manually process the transactional data in order to generate a custom report, if possible.

Moreover, even if the standard set of reports were inclusive of the desired report, typically these standard reports were only generated periodically and were typically provided via email in a static (un-modifiable) form. While the standard, static reporting approach included advantages over simply providing access to raw transactional data, difficulties in accessing and extracting the unique data desired by many users, in a user-friendly, manner remained unaddressed.

An embodiment provides a system architecture that provides a plurality of layers that in turn facilitate provision of real time source data availability. In an embodiment, the real time source data is made available to an analytics platform. The analytics platform offers a user friendly front end service that offers users role-based access to the source data. In an embodiment, a user may access operational data via the analytics platform to perform role based analysis and reporting based on the operational data.

Accordingly, an embodiment provides a system architecture that provides a plurality of layers that in turn facilitate provision of real time data availability. In an embodiment, the data of various sources, e.g., hospitals, departments, areas or units, etc., is made accessible to a front end service, e.g., Microsoft SharePoint® service, such that an end user may access the source data in a variety of ways. In an embodiment, the source data may be manipulated to be reported and viewed in a variety of ways without altering the source data. This permits end users, e.g., based on permissions, to view the source data (or sub-sets thereof) at varying degrees of granularity and in a variety of ways, and at any time, without altering the ultimate source data.

The illustrated example embodiments will be best understood by reference to the figures. The following description is intended only by way of example, and simply illustrates certain example embodiments.

An embodiment implements a system architecture that provides a plurality of layers that in turn facilitate provision of real time source data availability. In a source layer, each location, e.g., hospital, hospital department or unit/area, also referred to as a "tenant," is provided with a service such as the TELETRACKING XT system, illustrated at 101a, 101b. In a non-limiting example, a source layer device may be located on the premises. In an embodiment, one or more of the source layer devices may not be located on the premises. Each source layer device offers a service that acts to collect source data, e.g., transactional data such as number of admissions, etc., related to the site. The source level service provides source data that may be generated from an automated process, e.g., via RFID patient or equipment tracking, manually generated, or a combination of the foregoing.

The system architecture includes an integration layer that communicates with source layer devices 101a, 101b. The integration layer includes an integration service, e.g., implemented on a server such as a MICROSOFT BizTalk® server 103 with support database 102, that polls the source layer devices 101a, 101b for the source data. The integration layer server polls and receives the incoming source data and routes that data to an appropriate, e.g., tenant specific, staging database 104. For example, each tenant may have a separate staging database 104, for example hosted on a MICROSOFT SQL server.

A communication between the staging database(s) 104 and a warehouse layer, e.g., including tenant specific database 105 and data cube 106, provides storage of the source data derived from the tenants. The warehouse layer is formed such that a communication of the source data to a front end layer 107, e.g., implemented in Microsoft SharePoint®, is facilitated. Client devices may access a SharePoint® front end 107 to access the source data in a variety of ways, as further described herein.

Figure 2:
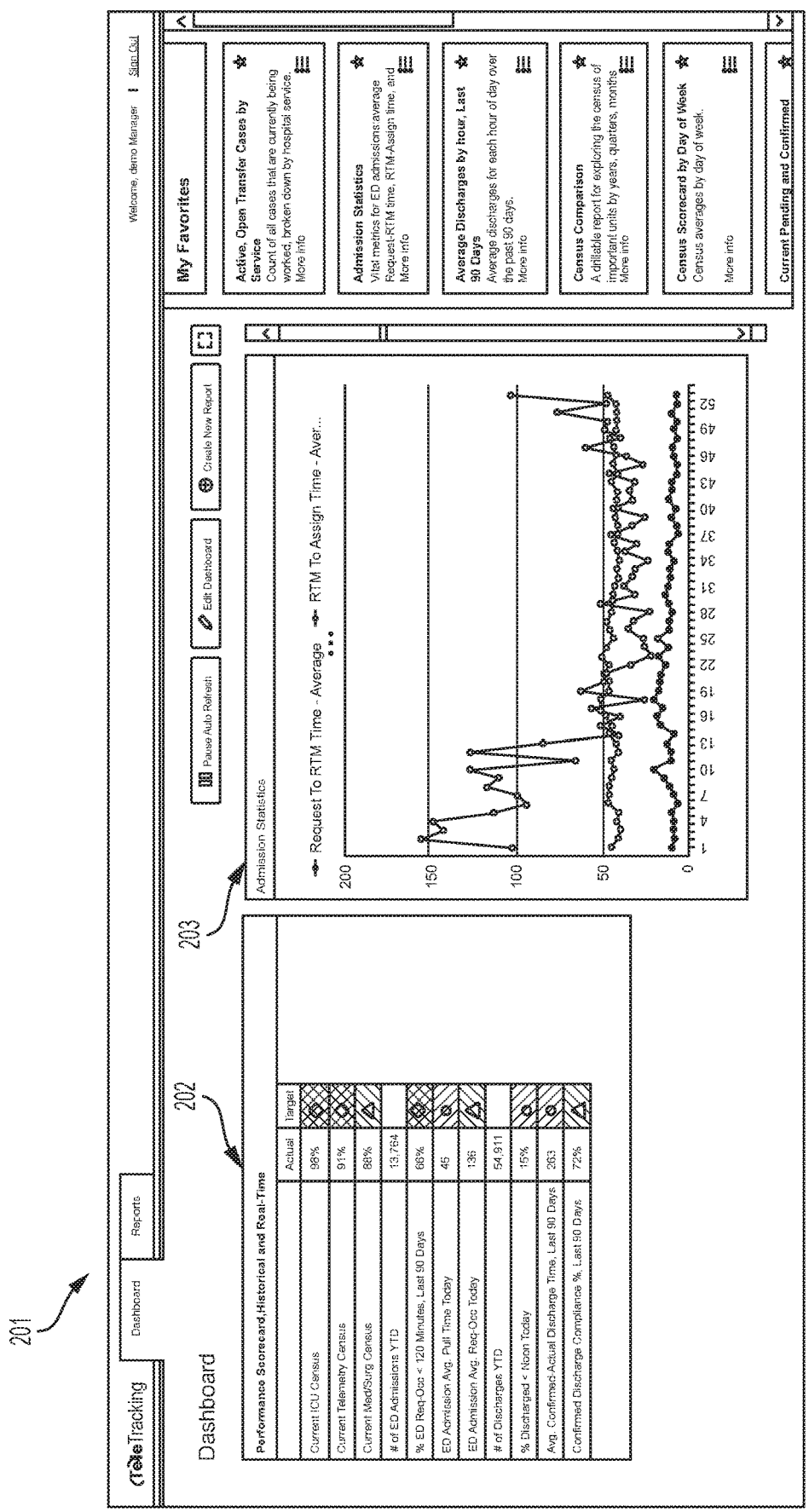
FIG. 2 illustrates an example screen view of a dashboard accessed by a client device.

FIG. 2 illustrates an example screen shot of dashboard 201, e.g., generated at a client device following access to a front end device 107. The dashboard 201 is a user interface that permits a user to access various reports, including the ability to generate new reports on the fly and the ability to drill down within data to reveal the source measurement data used in the reporting. The dashboard 201 may be configured to display certain reports responsive to a user login, e.g., from a "My Favorites" list or like section of the user interface.

Illustrated in FIG. 2, by way of example, is a tabular reporting of measurements provided at 202, in this example in the form of "Performance Scorecard, Historical and Real-Time." The measurement data, e.g., current number of ICU patients reported as a percentage, is retrieved from a source, e.g., source device 101a of FIG. 1. The table 202 lists various data measures such as "Current ICU Census," "# of ED Admissions YTD," "% Discharged<Noon Today," etc.

In a right part of the dashboard 201, indicated at 203, is a chart showing "Admission Statistics," which may be retrieved via clicking on or interacting with "Admission Statistics" in the "My Favorites" area. The chart reports (in line graph form here) on various measurement/source data regarding current admission statistics, e.g., for a particular hospital department, unit or area.

As may be appreciated, however, such tabular measurements 202 and 203 may be included in conventional, standard reports. However, a particular user may be interested in a view of the measurement data that is not provided according to one of the standard report types. Conventionally, such a user would have no resort but to access the source data, if permitted, and manually prepare an appropriate report or chart type. Moreover, typically a user would not be able to drill down within a table or chart in order to access the underlying hospital source data to glean further details regarding a particular reported measure, e.g., "% of ED Admissions YTD."

Figure 3:
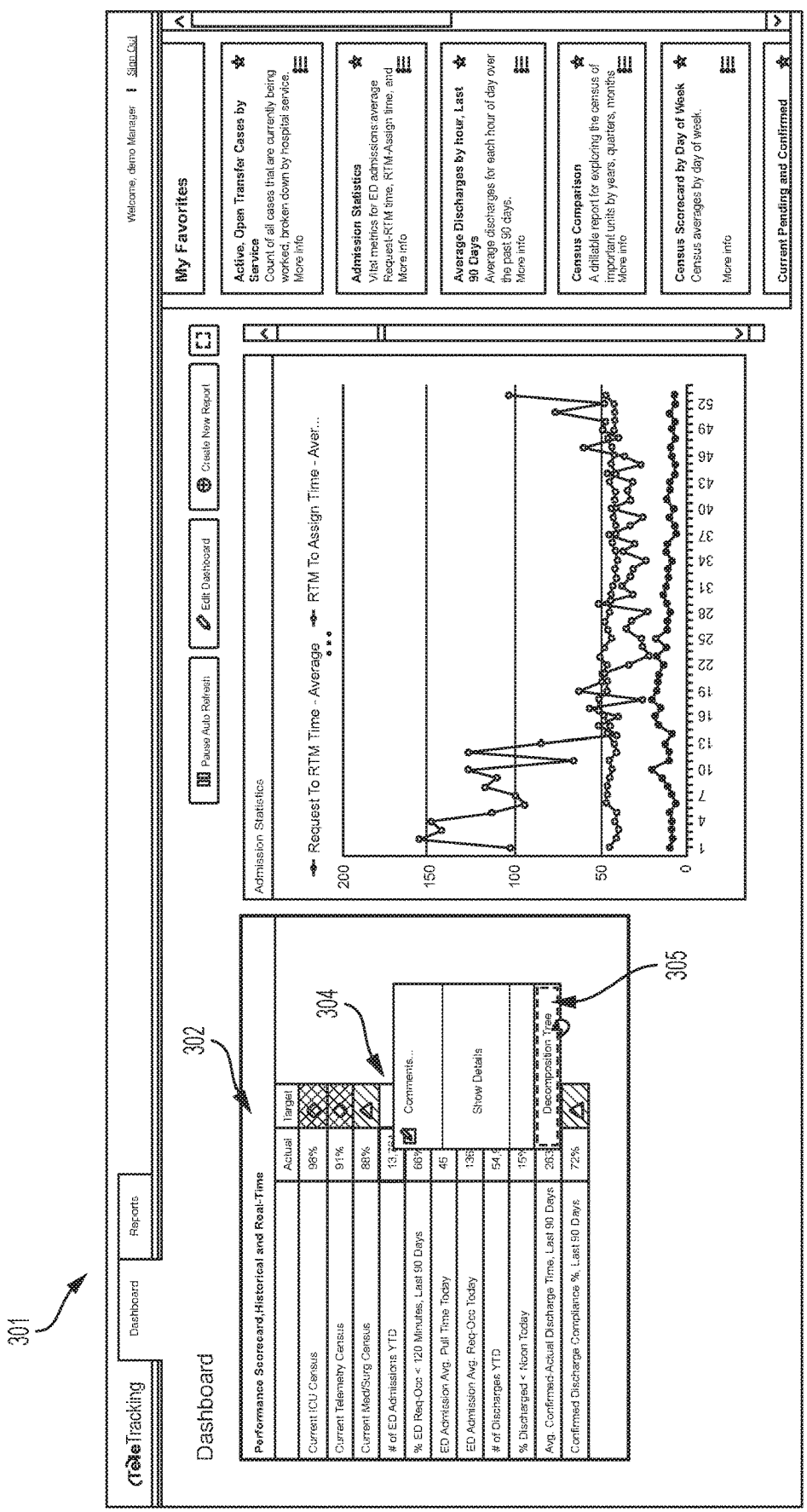
FIG. 3 illustrates a user interface offered by interfacing with functionally linked dashboard elements.

Thus, as illustrated in FIG. 3, an embodiment provides additional functionality via the dashboard 301 by virtue of how the source data is stored, organized, indexed and made accessible to end users, e.g., accessing the source data via a front end of the architecture, as illustrated in FIG. 1. For example, illustrated in FIG. 3 is a menu 304 that is opened, e.g., in response to a user interfacing with a particular cell of the table 302, in this example the measurement report for "# of ED admissions YTD." In the menu 304, options are provided, e.g., for decomposing the data via a decomposition tree option, illustrated at 305.

Figure 4:
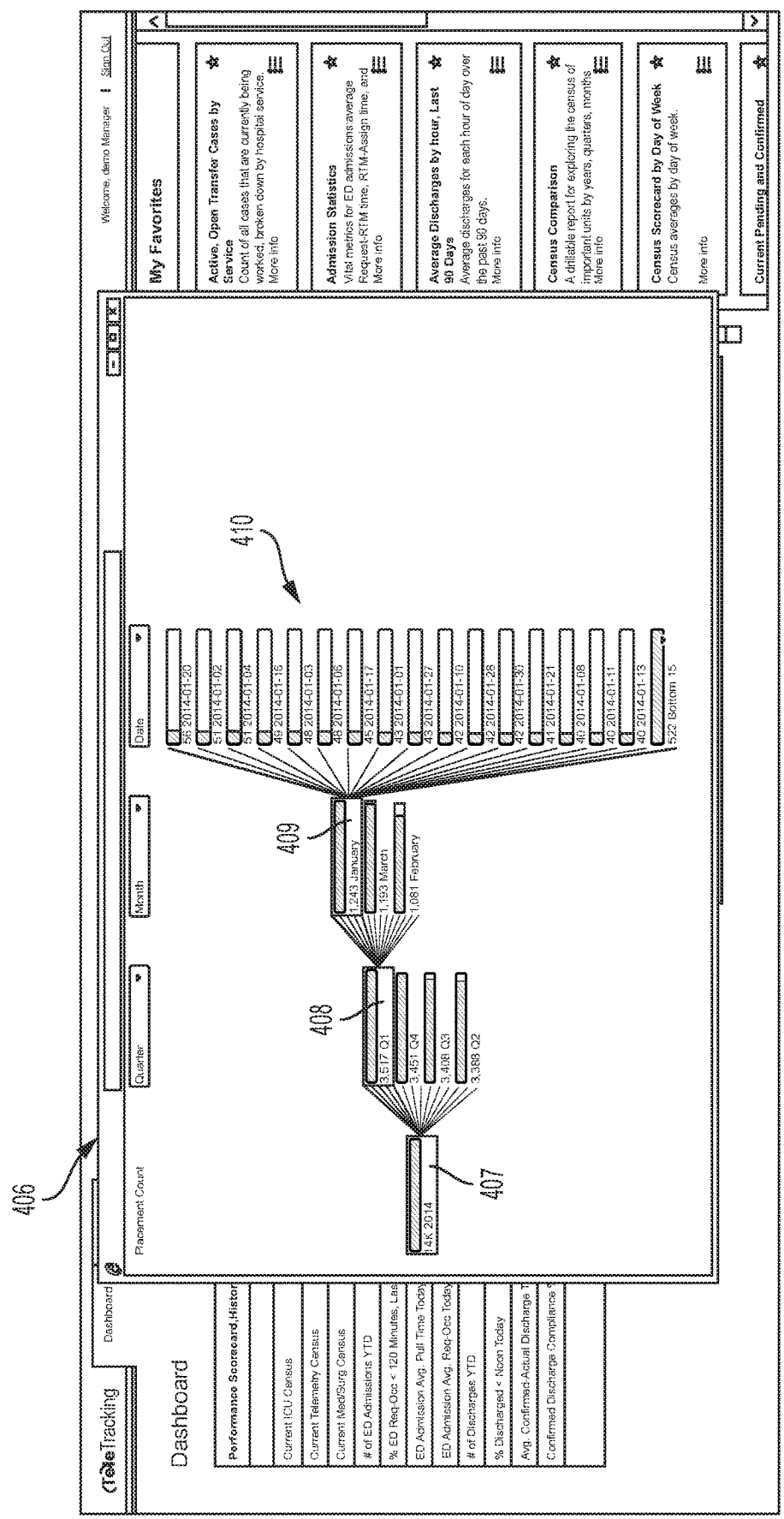
FIG. 4 illustrates an example of a decomposition tree interface.

As illustrated in FIG. 4, such interfacing with an executable element of the table 302 brings up an interactive view 406. This interactive view permits successive interaction with executable elements within the view 406 via selection of appropriate dimensions or filters such that further refined measurement/source data may be displayed regarding the initial cell's reported measurement value. In the current example, the "# of ED admissions YTD" is revealed to be based on 14K in the year 2014, as illustrated at 407. With user interaction with element 407 (and/or per a drop down or like function) to use a quarter dimension, it is further revealed that this 14K number for the year is the result of a particular quarterly breakdown, e.g., 3,517 in Q1, as illustrated at 408. Further user interaction with element 408 to a month dimension displays the months for Q1, i.e., January, February and March (here reoriented according to # of ED admissions, greatest to fewest), with 1,243 ED admissions for January, as illustrated by element 409. In turn, interacting with element 408 provides a further refined list, here by date for the month of January, as illustrated at 410. Therefore, the user is able to retrieve the source data, e.g., from warehouse layer of the system architecture, via simple interface with any active element provided to select a dimension of interest. This allows a user to easily access, at varying levels of granularity, the source data that was used to create the reported measure.

An embodiment facilitates such drill down operations by virtue of implementing real time source data collection, e.g., via a service located at each physical location, as illustrated at source level in FIG. 1, and via linking the source data to functional dimensions that are displayed via the front end, as illustrated at front end level in FIG. 1. By way of example, an embodiment links the source data regarding the ED admission raw data to a time dimension, which then may be utilized as shown in FIG. 3 and FIG. 4 to drill down into the ED admission source data to reveal further refined source data making up the reported measure, YTD ED admissions refined by quarters, months, and days in the example used thus far.

Figure 5:
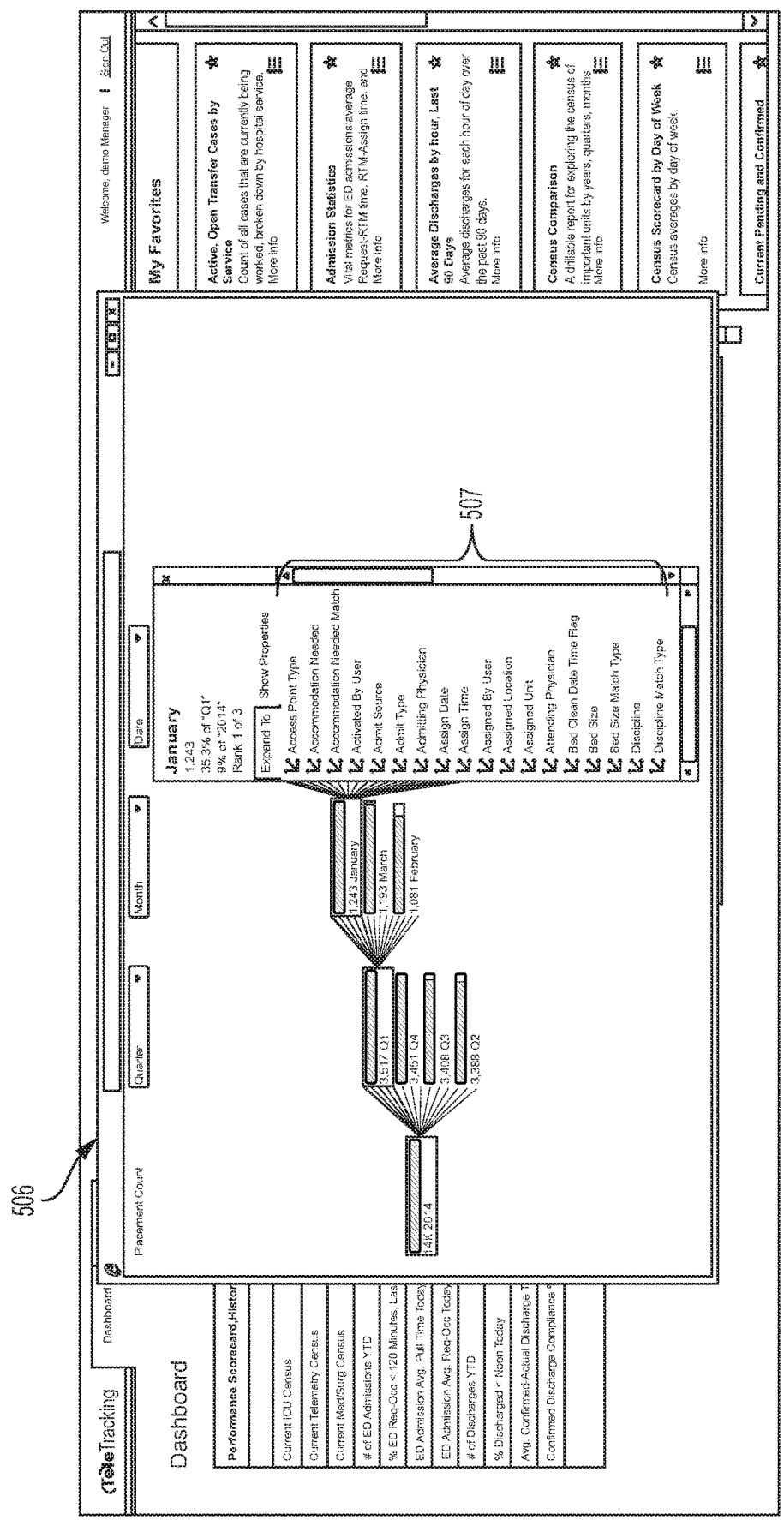
FIG. 5 illustrates example dimensions associated with source data of the system.

Furthermore, additional functional dimensions are provided by an embodiment, as illustrated in the example of FIG. 5. An embodiment has access to source data according to a plurality of dimensions, some of which are indicated at 507 of FIG. 5. The example dimensions 507 illustrated here are accessible from the view 506 and correspond to available dimensions for the ED admission source data collected for January, 2014. A user may select one or more of the dimensions to sort (here in an "expand by" function) the source data, e.g., stored in warehouse layer of the architecture, as illustrated in FIG. 1. This permits the user to easily expand the display to more granular source data without affecting the underlying source data.

Figure 6:
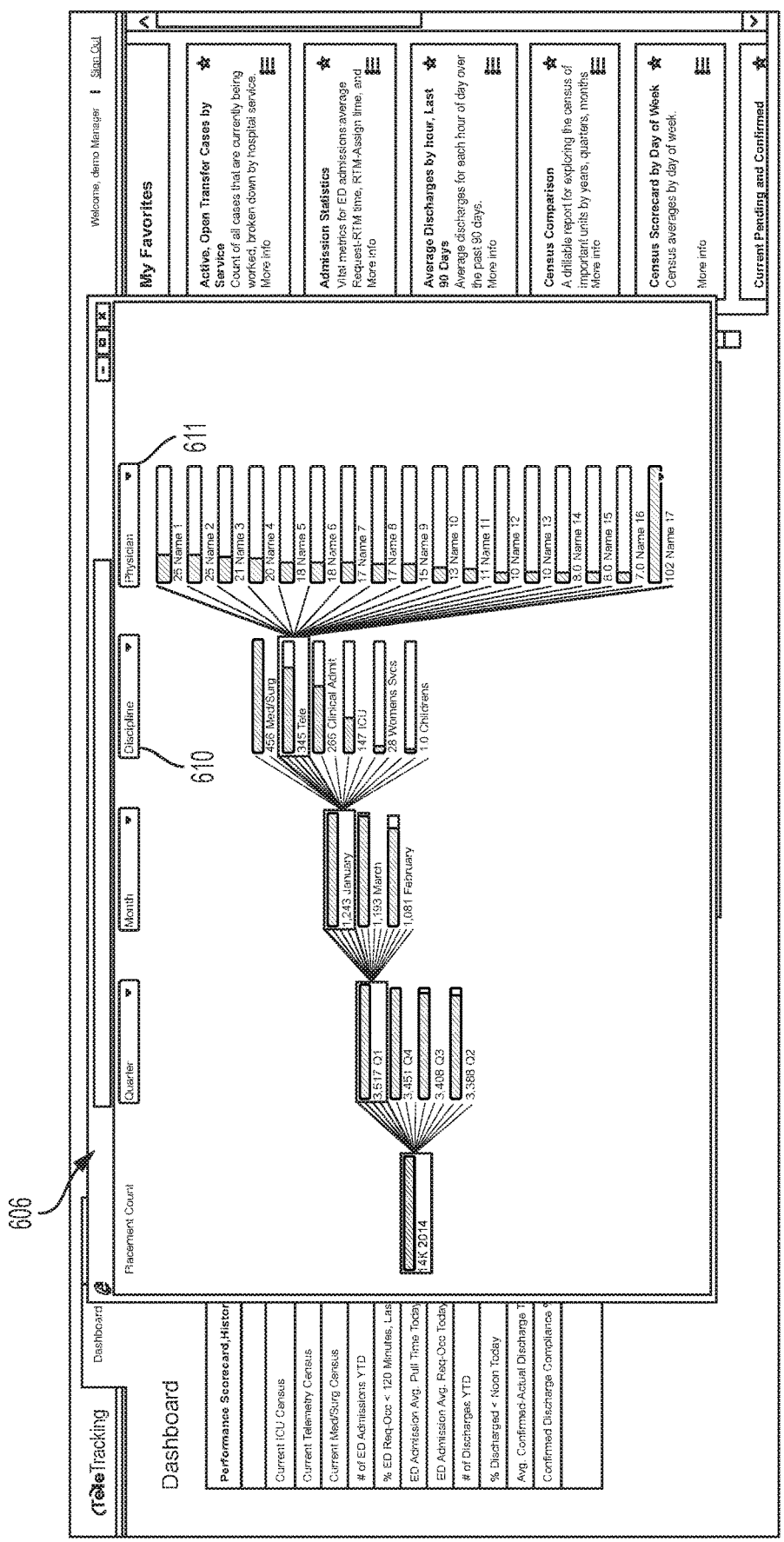
FIG. 6 illustrates an example decomposition tree sorted according to user selected dimensions.

A user may choose from among the plurality of dimensions for accessing different source data in a drill down operation, as illustrated in the example of FIG. 6. Here, the view provided to the user has changed, although the initial cell, i.e., "# of ED admissions YTD," has not changed. In the example illustrated in FIG. 6, the user has again selected yearly, quarterly and monthly dimensions; however, the user has instead chosen discipline 610 and physician 611 dimensions. This results in an altered display of different source data, i.e., the physicians assigned to ED admissions, sorted by discipline, for the month of January, 2014. As may be appreciated then, source data reporting and appropriate data warehousing techniques are fundamental to the resultant capability in the dashboard.

Figure 7:
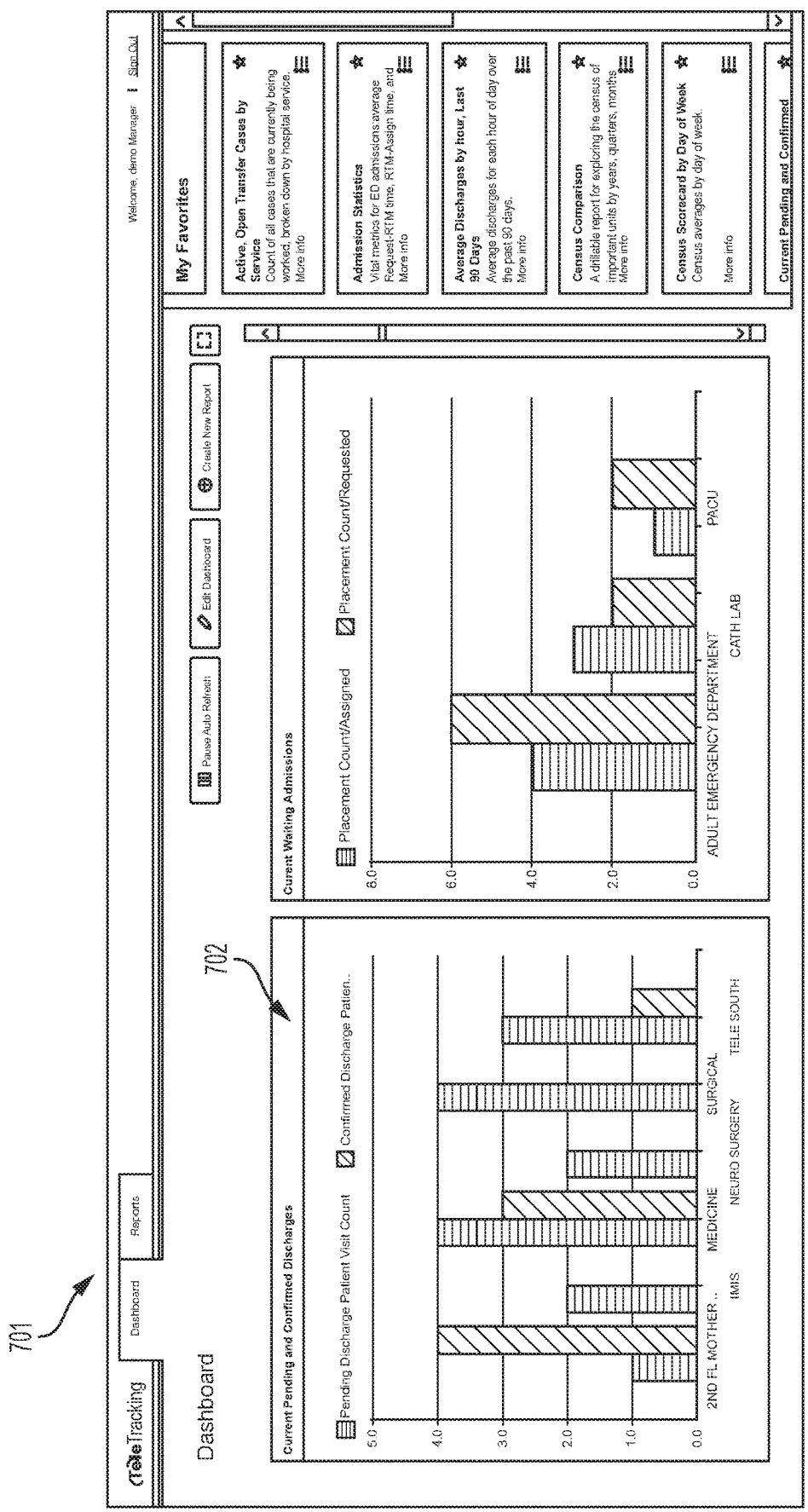
FIG. 7 illustrates example charts displayed in a dashboard view.

Turning to FIG. 7, an embodiment provides a dashboard view 701 in which a chart 702 for "Current Pending and Confirmed Discharges" is displayed. As with other reported measures, the confirmed pending and confirmed discharge source data is retrieved from the site(s) and displayed in a chart as number vs. area (e.g., IMIS, Medicine, Surgical, etc.). The user may easily interact with the chart in order to drill down within the reported measures without interfering with the source data (and the views provided to other users).

Figure 8:
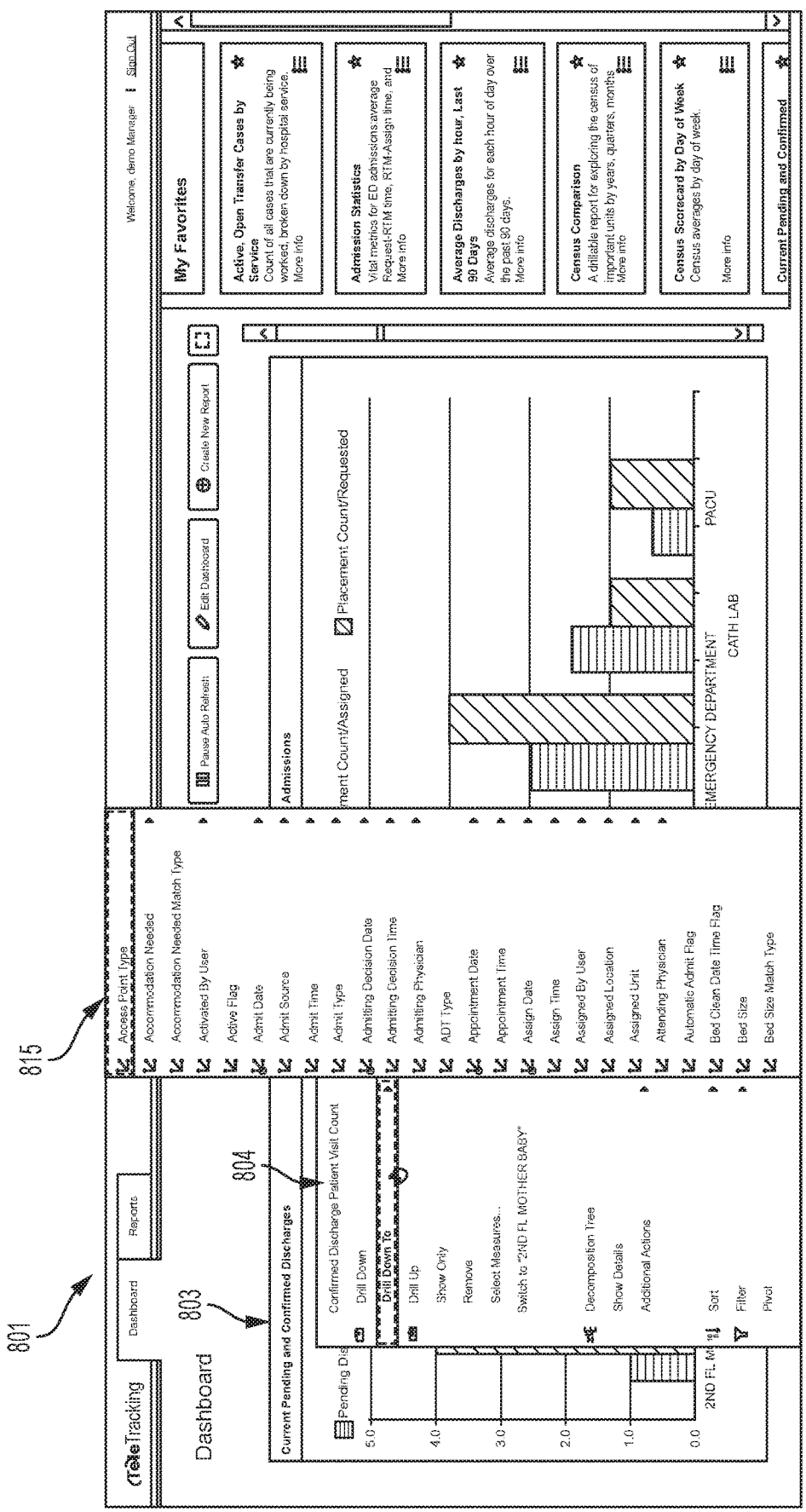
FIG. 8 illustrates an example of a drill down user interface displayed after interfacing with a chart element.

For example, as illustrated in FIG. 8, if a user interfaces with a chart 803 in the dashboard view 801, an interactive menu 804 is provided. Here, the interactive menu 804 provides a plurality of options, one of which is "Drill Down to." If a user interfaces with this option in the menu 804, a listing of options is provided at 807, i.e., dimensions with which the user may drill down to the filter or refine the source data used to prepare the chart 803.

Figure 9:
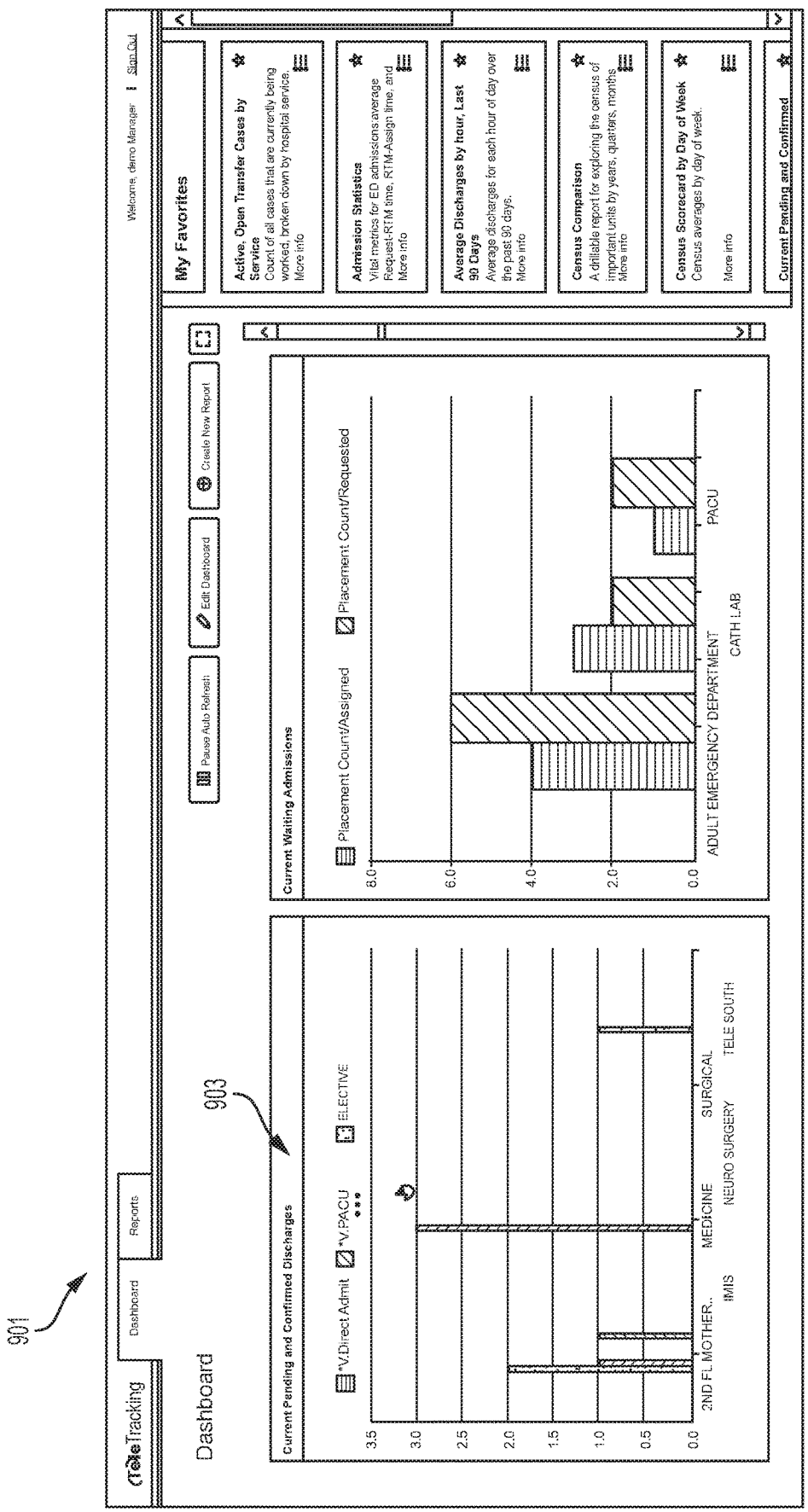
FIG. 9 illustrates an example of an updated chart after a drill down according to FIG. 8.

Thus, as illustrated in FIG. 9, if the user selects a different option, e.g., "access point type," as shown in FIG. 8, the chart is reformed automatically and displayed using the source data for a chart 903, i.e., showing current pending and confirmed discharges by access point type (here, Direct Admit, PACU and Elective) for each of the areas, again in a number vs. area configuration. The user is therefore permitted to create a new chart on the fly with little more involvement with the source data than selecting which source data to display in the chart 903. An embodiment automatically selects the underlying source data to pull for the chart based on the active chart settings, e.g., as informed by the user selection(s) of dimensions offered by virtue of system architecture, i.e., warehousing of the source data with user selectable dimensions.

Figure 10:
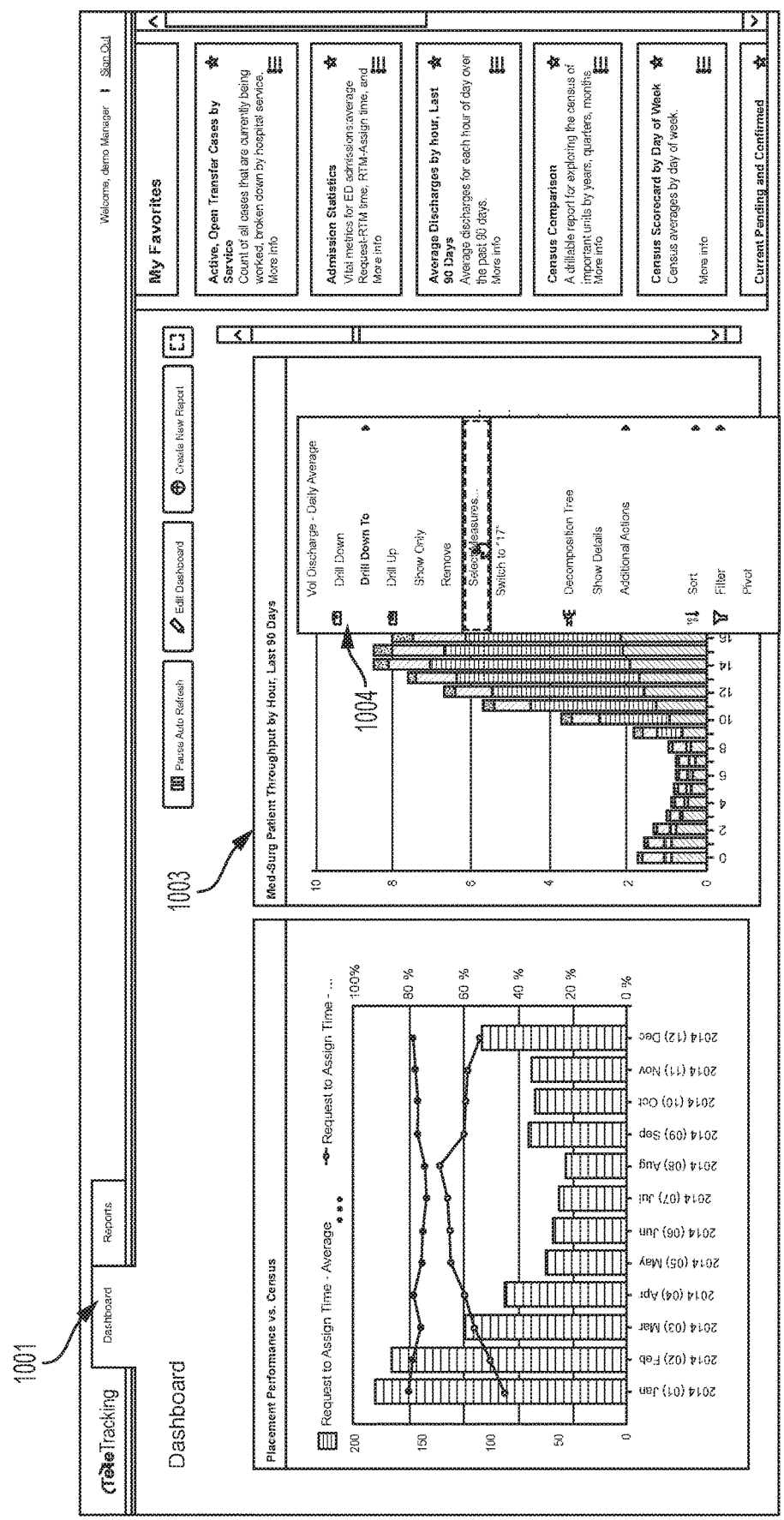
FIG. 10 illustrates an example of selecting measures via interface with a functional chart element.

A user may select the measures with which a chart or other data report (e.g., data table) is compiled. By way of example, FIG. 10 illustrates that a user may interface with a chart 1003 displayed in the dashboard view 1001, e.g., by right clicking or otherwise interfacing on the chart 1003, to bring up a menu 1004. Here, the menu 1004 (similar to menu 804) permits the user to select active chart options.

Figure 11:
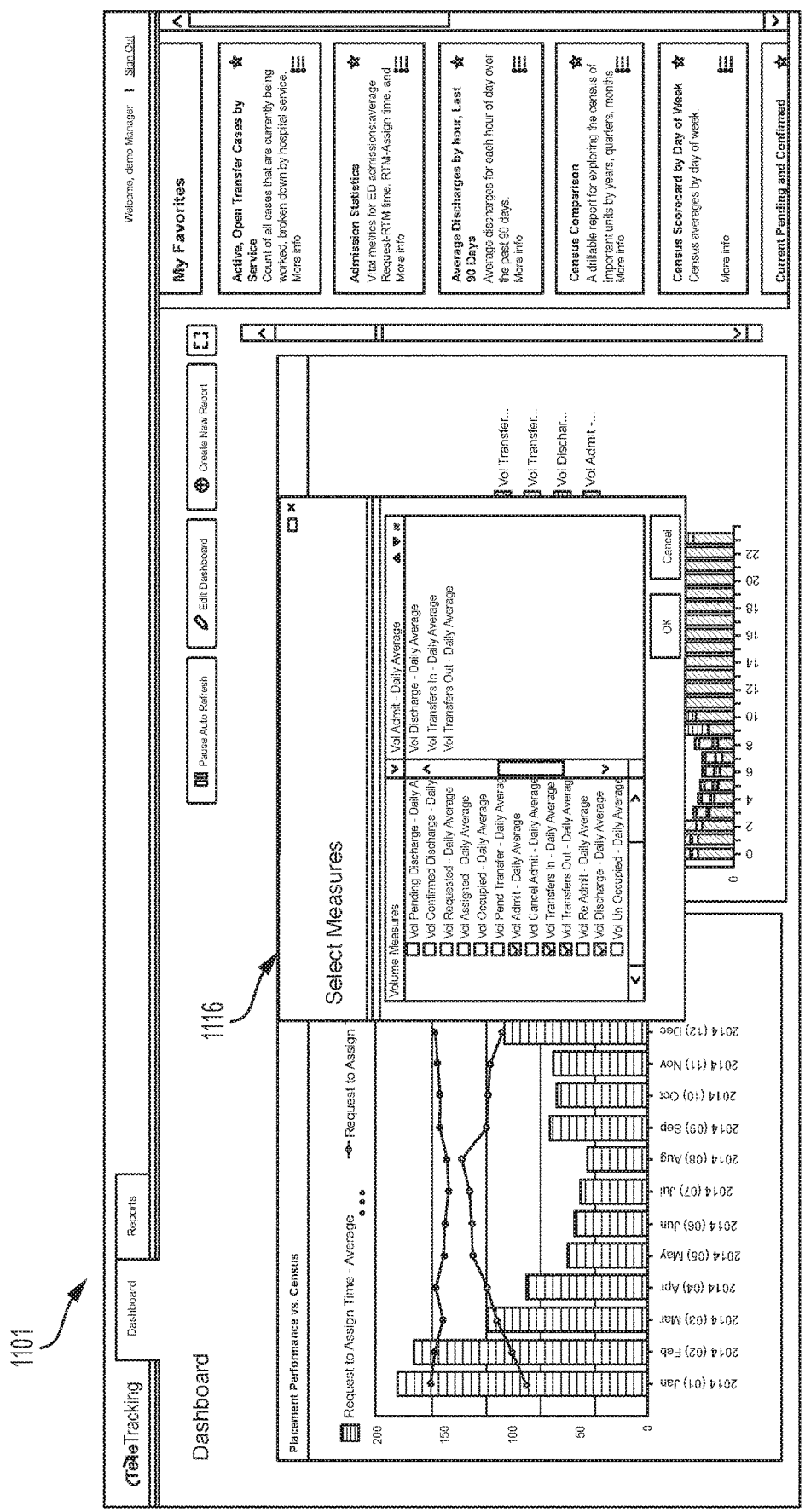
FIG. 11 illustrates an example of a measure selection interface.

For example, if the user provides input to the "Select Measures" option in the menu 1004, a user is provided with a display interface 1116, illustrated in the dashboard 1101 of FIG. 11. Here, the display interface 1116 provides the user an opportunity to select the measures, e.g., Vol. Admit Daily Average, with which the chart is to be formed. Depending on the user's selection in interface 1116, the chart will change form by virtue of an embodiment pulling different source data, i.e., related to the measure(s) selected.

Figure 12:
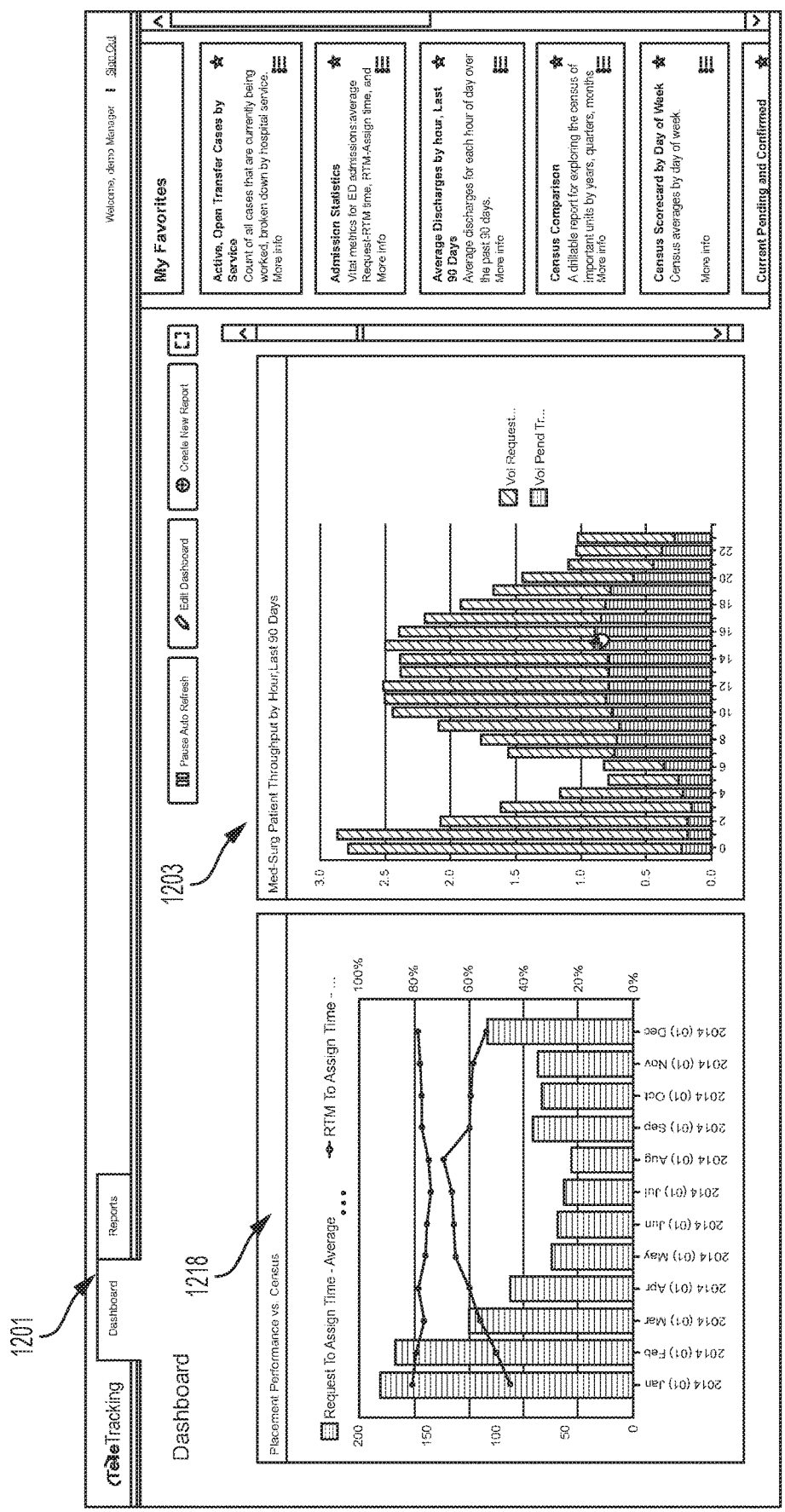
FIG. 12 illustrates an example of an updated chart according to selected measures.

Thus, as shown in FIG. 12, a user may have selected Voluntary Pend Transfer—Daily Average and Voluntary Requested—Daily Average from interface 1116 of FIG. 11. In this case, the system will pull the source data, e.g., from data warehouse as illustrated in FIG. 1, to provide a chart 1203, i.e., displaying reported values for these measures in the chart rather than the measures of chart 1003 of FIG. 10. Thus, an embodiment permits a user to view the measures desired in the chart based on the underlying source data stored in the warehousing architecture.

A user may also view the source data used to prepare the chart directly.

Figure 13:
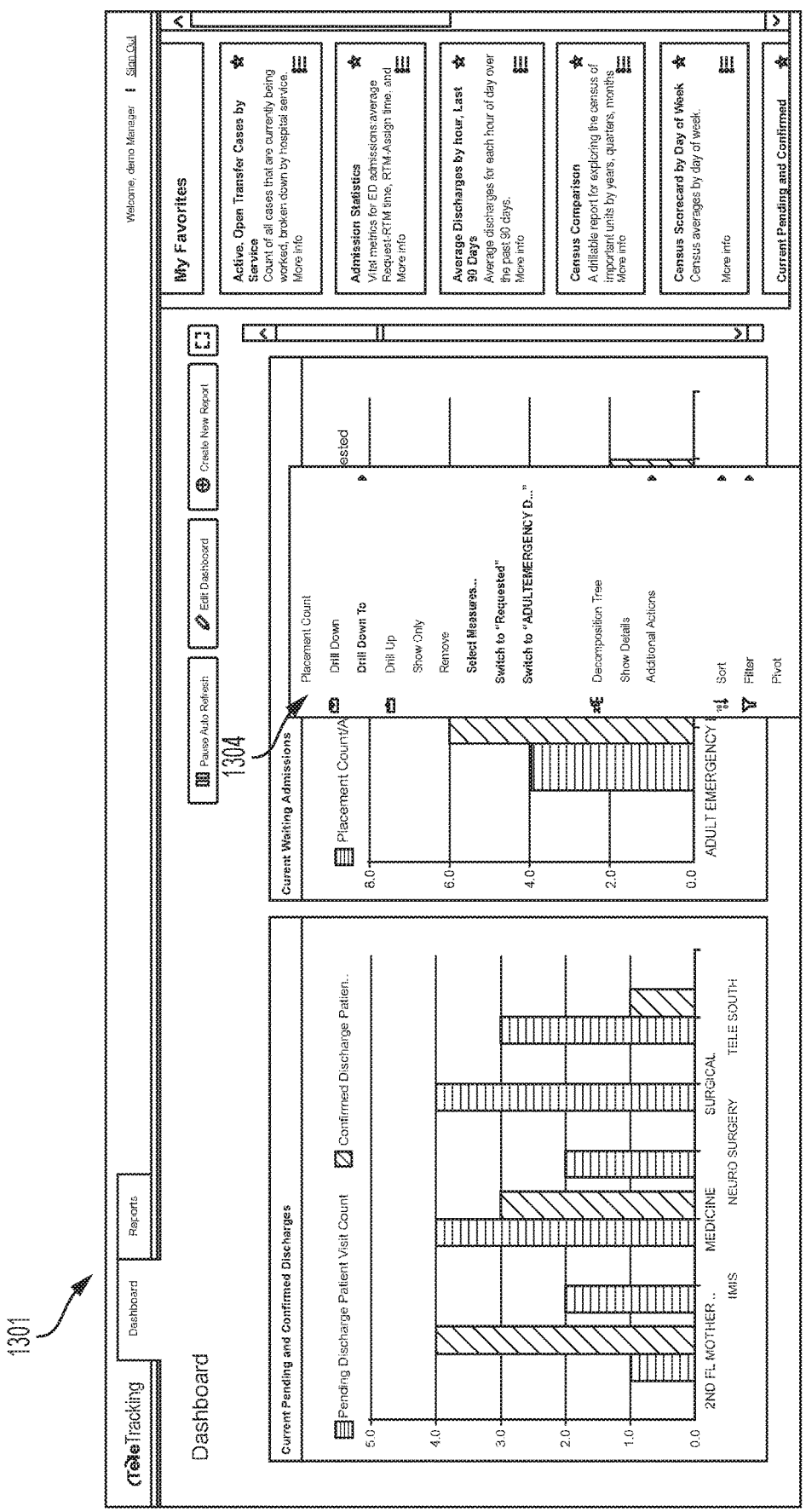
FIG. 13 illustrates an example of a menu interface for viewing detailed source data associated with a chart.
Figure 14:
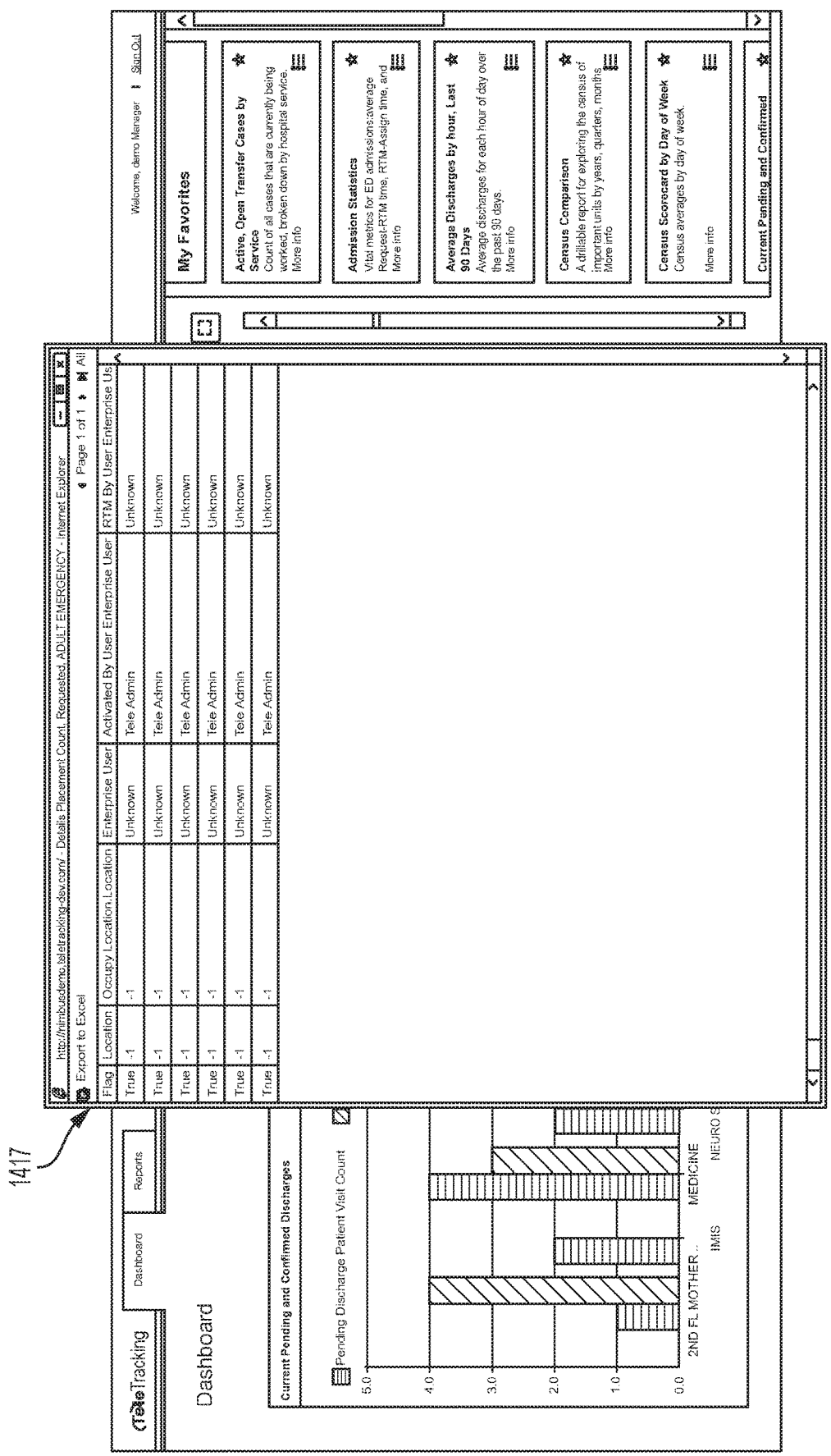
FIG. 14 illustrates an example of detailed source data.

In an embodiment, this may be facilitated by linking a particular user (e.g., via login credential) to a given level of access to source data within the system. In an embodiment, the access to the source data may be read-only access. By way of example, illustrated in FIG. 13 is a dashboard view 1301 in which a user has interfaced with a chart, e.g., via right clicking or otherwise interfacing with the rightmost chart in the dashboard, i.e., "Current Waiting Admissions" in this example, to bring up a menu 1304. If the user wishes to explore the underlying source data that was used to generate this chart, i.e., the source data corresponding to a location's or area's current waiting admissions, a user may bring up the menu 1304 and select a "Show Details" option. In response to this selection an embodiment retrieves the source data, in this example the source data regarding the current waiting admissions, as illustrated in detailed data view 1417 of FIG. 14 (the detailed data view in this example includes example data for illustration purposes only). This enables the user to view the detailed source data, e.g., to determine why there are or are not current waiting admissions within an area, e.g., hospital area or department.

An embodiment permits a variety of filtering techniques to be employed such that a user may customize the views (e.g., charts, tables, etc.,) of the reported data to fit his or her needs. This is again possible because the data is collected from the sources and warehoused in an intelligent fashion such that various dimensions are associated with the source data, making retrieval of sub-sets of the source data user friendly.

Figure 15:
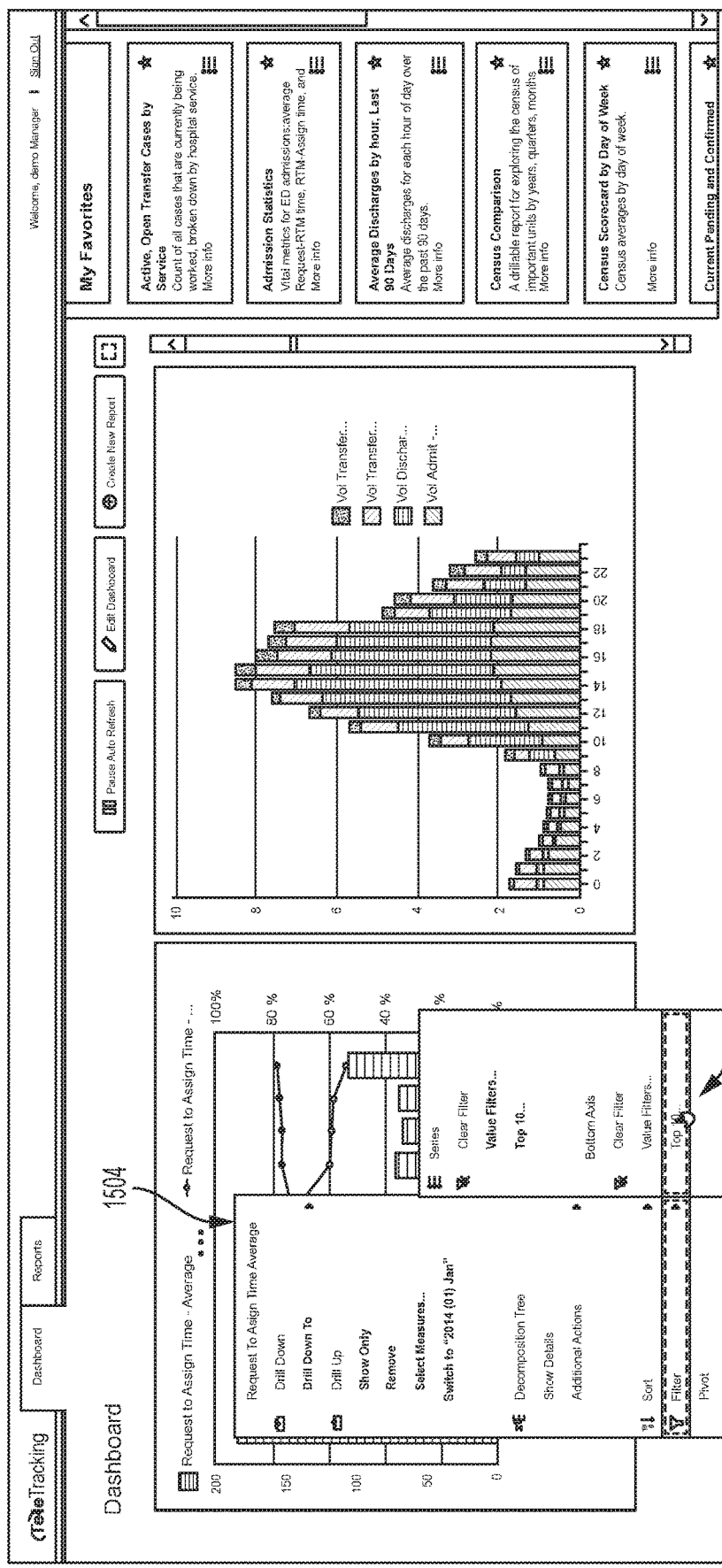
FIG. 15 illustrates an example of a filtering menu and sub menu.

For example, as illustrated in FIG. 15, should a user wish to view a filtered version of a chart provided in a dashboard, e.g., a version of chart 1203 of FIG. 12 filtered in a different way, a user may again simply interface with the chart 1203 to bring up a menu 1504 offering filtering options, as illustrated in FIG. 15. If a user selects a filtering option, a sub menu 1518 may be displayed providing various filtering options. The filtering options influence which source data is included in the chart. Thus, chart 1203 originally pulled source data from the system, e.g., warehouse as illustrated in FIG. 1, for "Request to Assign Time—Average," which was reported in chart 1203 as the monthly average (aggregate) for the entire year of 2014. However, a user may wish to view a "top n" (e.g., top 10, top 5, etc.) months of 2014, e.g., in terms of request to assignment time, as illustrated by the selection from sub menu 1518.

Figure 16:
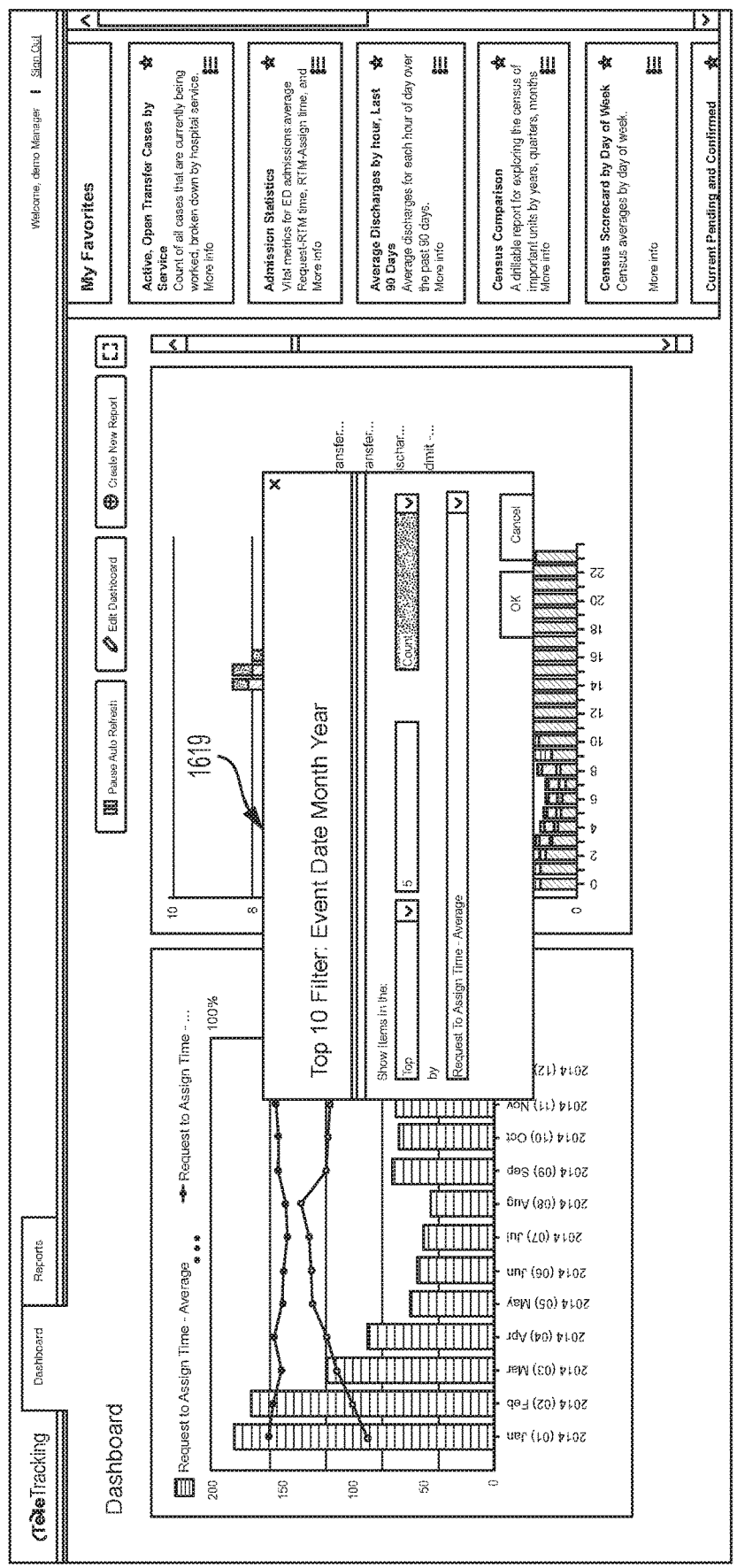
FIG. 16 illustrates an example of a filtering interface.
Figure 17:
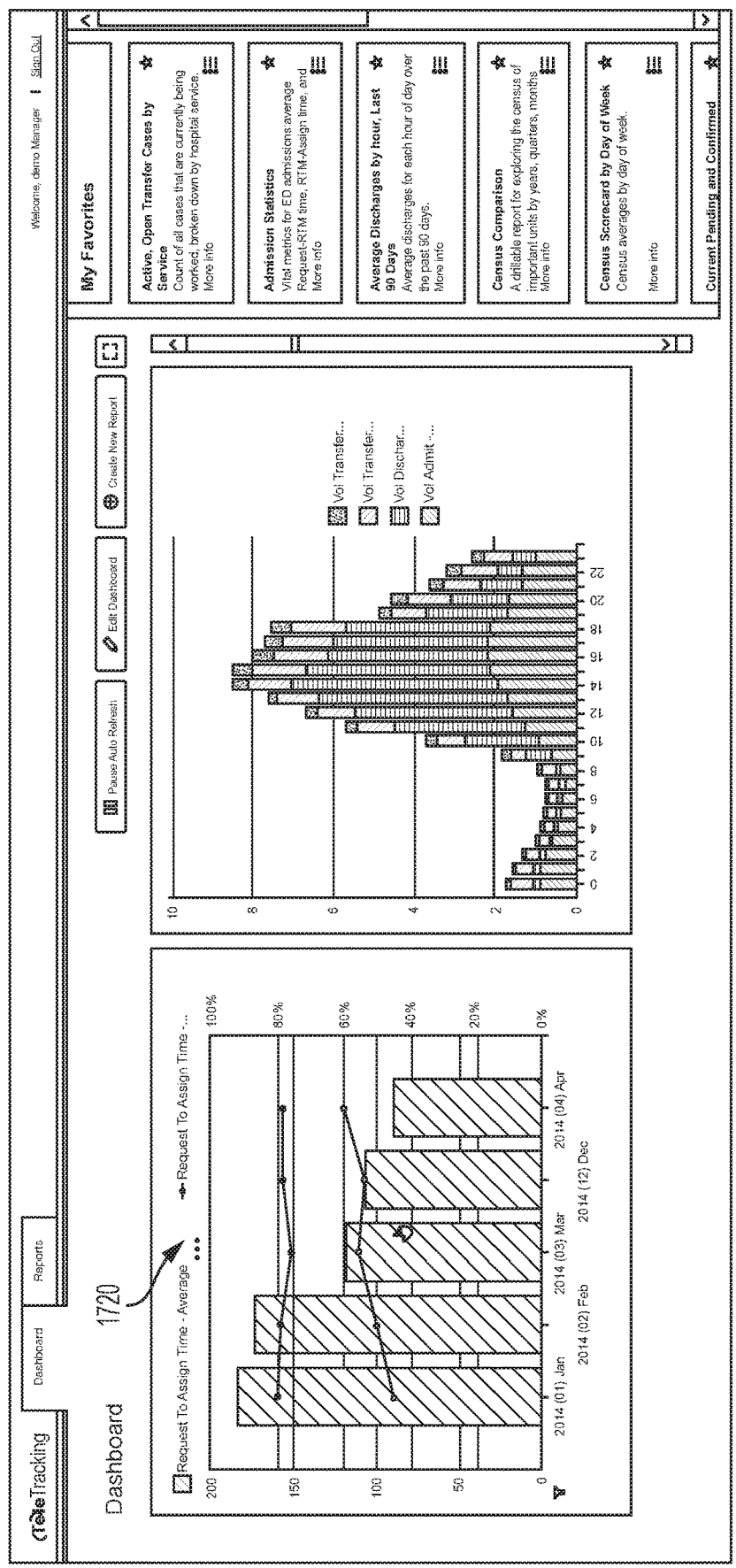
FIG. 17 illustrates an example of an updated chart responsive to filtering.

In response to the user selection at sub menu 1518, an embodiment may provide a user interface 1619, as illustrated in FIG. 16. Here, the user is provided with the opportunity to customize the filtering options. In this example, the user has selected to view the top 5 (count) by request to assign time—average, which will retrieve the top five (5) months in terms of their counts for request to assign time—average values. This is illustrated in the updated chart, i.e., chart 1720 of FIG. 17. It will be appreciated that chart 1720 has changed from that of chart 1203, where the chart 1720 now only includes the top 5 months (December, January, February, March and April) with the highest average request to assign times. As may be appreciated, this permits the user to easily reorganize the charts to display source data of interest from the central system.

While various other circuits, circuitry or components may be utilized in information handling devices, with a computer, server, client device or the like participating in the architecture outlined in FIG. 1, an example device that may be used in implementing one or more embodiments includes a computing device in the form of a computer 1800. This example device may be a server used in one of the systems in a hospital network, or one of the remote computers connected to the hospital network. Components of computer 1800 may include, but are not limited to, a processing unit 1820, a system memory 1830, and a system bus 1822 that couples various system components including the system memory 1830 to the processing unit 1820. Computer 1800 may include or have access to a variety of computer readable media, including databases. The system memory 1830 may include non-signal computer readable storage media, for example in the form of volatile and/or nonvolatile memory such as read only memory (ROM) and/or random access memory (RAM). By way of example, and not limitation, system memory 1830 may also include an operating system, application programs, other program modules, and program data.

A user can interface with (for example, enter commands and information) the computer 1800 through input devices 1850. A monitor or other type of device can also be connected to the system bus 1822 via an interface, such as an output interface 1860. The computer may include a database 1840, e.g., if it is part of the warehouse layer in FIG. 1. In addition to a monitor, computers may also include other peripheral output devices. The computer 1800 may operate in a networked or distributed environment using logical connections to one or more other remote device(s) 1880 such as other computers. The logical connections may include network interface(s) 1870 to a network, such as a local area network (LAN), a wide area network (WAN), and/or a global computer network, but may also include other networks/buses.

Figure 18:
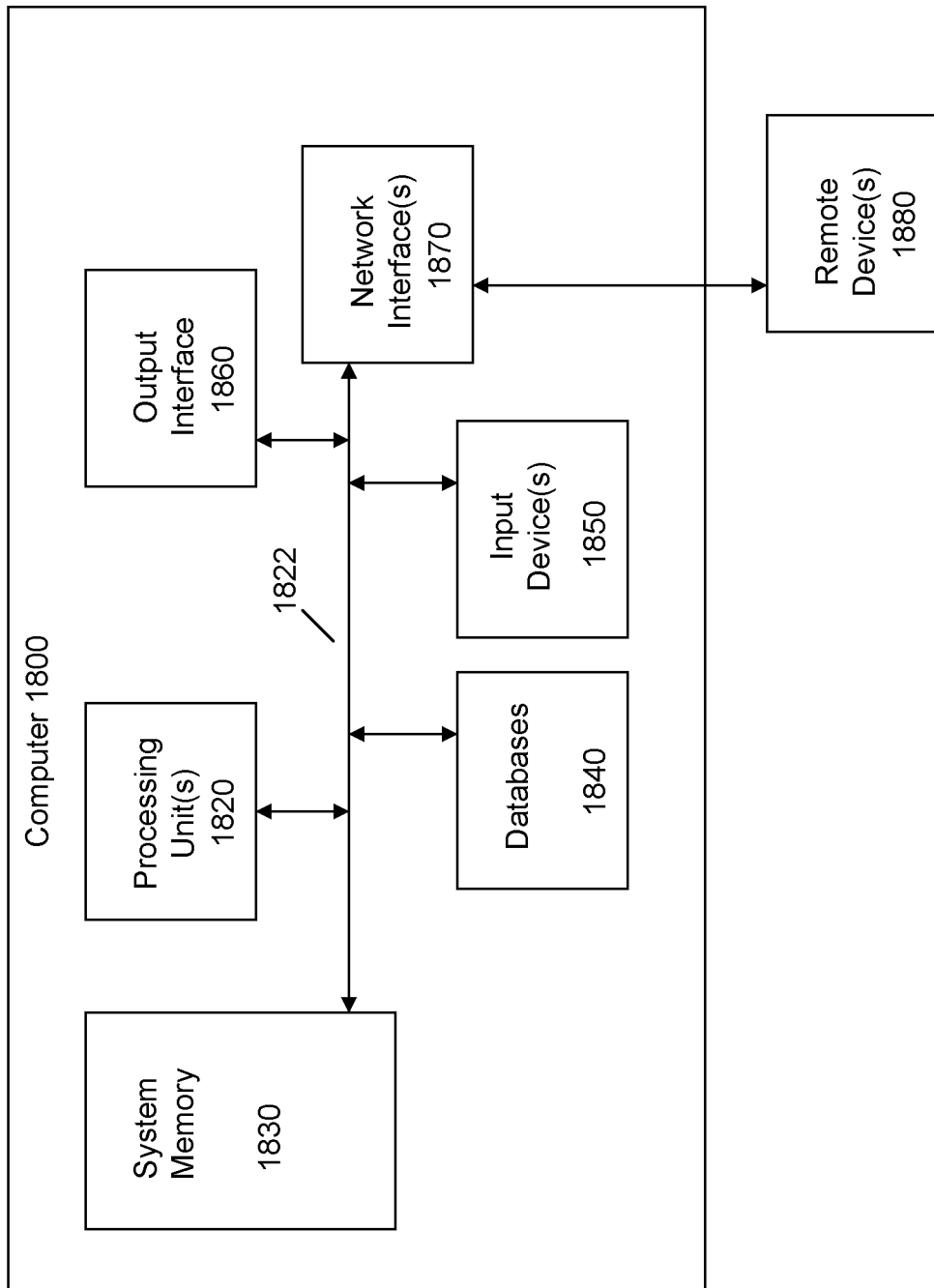
FIG. 18 illustrates an example of device circuitry.

Information handling device circuitry, as for example outlined in FIG. 18, may be used in client devices such as a personal desktop computer, a laptop computer, or smaller devices such as a tablet or a smart phone. In the latter cases, i.e., for a tablet computer and a smart phone, the circuitry outlined in FIG. 18 may be adapted to a system on chip type circuitry. The device, irrespective of the circuitry provided, may provide and receive data to/from another device, e.g., a server or system that coordinates with various other systems, e.g., as outlined in FIG. 1. As will be appreciated by one having ordinary skill in the art, other circuitry or additional circuitry from that outlined in the example of FIG. 18 may be employed in various electronic devices that are used in whole or in part to implement the systems, methods and products of the various embodiments described herein.

As will be appreciated by one skilled in the art, various aspects may be embodied as a system, method or device program product. Accordingly, aspects may take the form of an entirely hardware embodiment or an embodiment including software and hardware that may all generally be referred to herein as a "circuit," "module" or "system." Furthermore, aspects may take the form of a device program product embodied in one or more device readable medium(s) having device readable program code embodied therewith.

Any combination of one or more non-signal device readable storage medium(s) may be utilized. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), a portable compact disc read-only memory (CD-ROM), a magnetic storage device, or any suitable combination of the foregoing. In the context of this document, a storage medium is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, or through a hard wire connection.

Example embodiments are described herein with reference to the figures, which illustrate example methods, devices and program products according to various example embodiments. It will be understood that the actions and functionality may be implemented at least in part by program instructions. These program instructions may be provided to a processor of a device to create a special purpose information handling device such that the instructions, which execute via a processor of the device, implement the functions/acts specified.

It is worth noting that while specific blocks (or other illustrated elements or text) are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A system, comprising:
a plurality of devices associated with a site within a hospital facility, each of the plurality of devices providing event data, wherein the event data comprise transactional data identifying information related to statistics of the site and generated utilizing a statistic tracking system;
one or more source devices that store, in electronic memory, the event data provided by the plurality of devices;
a processor that operates to route the event data to a warehouse database, wherein to route comprises routing the event data to a portion of the warehouse database associated with the site;
said warehouse database storing the event data according to a plurality of storage dimensions associated with one or more of a plurality of selectable elements of a graphical user interface, each of the plurality of storage dimensions comprising a different refinement of information associated with the selectable element; and
a front end program that displays the graphical user interface having the plurality of selectable elements, wherein the graphical user interface allows a user to generate one or more reports using at least a portion of the event data;
wherein, responsive to user interface with one of the plurality of selectable elements in the graphical user interface, the data warehouse communicates a subset of the event data by associating a storage dimension with the one of the selectable elements in the graphical user interface, wherein the subset of event data comprises a refinement of the event data corresponding to the refinement of the associated storage dimension.

2. The system of claim 1, wherein the warehouse database communicates with the one or more source devices to obtain the event data according to a policy.

3. The system of claim 2, wherein the policy is a timing policy that provides near real-time updates of event data to the warehouse database.

4. The system of claim 1, wherein the plurality of storage dimensions are each associated with at least one of the plurality of selectable elements of the graphical user interface.

5. The system of claim 4, wherein each of the plurality of selectable elements of the graphical user interface is provided in a set of predetermined categories provided by the front end program.

6. The system of claim 1, wherein a subset of the plurality of selectable elements of the graphical user interface includes predetermined categories associated with a decomposition tree provided by the front end program.

7. The system of 1, wherein the graphical user interface provides an option to retrieve the event data.

8. The system of claim 1, wherein the front end program permits re-organization of the plurality of selectable elements to facilitate retrieval of different combinations of event data from the data warehouse.

9. The system of claim 1, wherein the front end program automatically forms a predetermined graphic using the event data based on one or more selectable elements selected by a user within the graphical user interface.

10. The system of claim 1, wherein:
the front end program determines a user permission; and
the front end program provides, based on the user permission, a predetermined view the event data associated with a predetermined subset of storage dimensions.

11. A method, comprising:
receiving, from a plurality of devices associated with a site within a hospital facility, event data, wherein the event data comprise transactional data identifying information related to statistics of the site and generated utilizing a statistic tracking system;
storing, in electronic memory of one or more source devices, event data reported by the plurality of devices;
routing, using a processor, the event data to a warehouse database, wherein the routing comprises routing the event data to a portion of the warehouse database associated with the site;
storing, in the warehouse database, the event data according to a plurality of storage dimensions associated with one or more of a plurality of selectable elements of a graphical user interface, each of the plurality of storage dimensions comprising a different refinement of information associated with the selectable element; and displaying, on a display device operatively coupled to the warehouse database, a front end program comprising the graphical user interface having the plurality of selectable elements, wherein the graphical user interface allows a user to generate one or more reports using at least a portion of the event data;

wherein, responsive to user interface with one of the plurality of selectable elements in the graphical user interface, the data warehouse communicates a subset of the event data by associating a storage dimension with the one of the selectable elements in the graphical user interface, wherein the subset of event data comprises a refinement of the event data corresponding to the refinement of the associated storage dimension.

12. The method of claim 11, wherein the warehouse database communicates with the one or more source devices to obtain the event data according to a policy.

13. The method of claim 12, wherein the policy is a timing policy that provides near real-time updates of tracking data to the warehouse database.

14. The method of claim 11, wherein the plurality of storage dimensions are each associated with at least one of the plurality of selectable elements of the graphical user interface.

15. The method of claim 14, wherein each of the plurality of selectable elements of the graphical user interface is provided in a set of predetermined categories provided by the front end program.

16. The method of claim 11, wherein a subset of the plurality of selectable elements of the graphical user interface includes predetermined categories associated with a decomposition tree provided by the front end program.

17. The method of 11, wherein the graphical user interface provides an option to retrieve the event data.

18. The method of claim 11, wherein the front end program permits re-organization of the plurality of selectable elements to facilitate retrieval of different combinations of event data from the data warehouse.

19. The method of claim 11, wherein the front end program automatically forms a predetermined graphic using the event data based on one or more selectable elements selected by a user within the graphical user interface.

20. The method of claim 11, further comprising:

determining a user permission;

wherein said front end program provides, based on the user permission, a predetermined view the event data associated with a predetermined subset of storage dimensions.

* * * * *